| United States Patent [19] | [11] | 4,096,165 |
|---|---|---|
| Meyers | [45] | Jun. 20, 1978 |

[54] METHOD OF MANUFACTURING AROMATIC ISOCYANATES

[75] Inventor: Bernard A. Meyers, East Brunswick, N.J.

[73] Assignee: Allied Chemical Corporation, Morris Township, N.J.

[21] Appl. No.: 737,822

[22] Filed: Nov. 1, 1976

[51] Int. Cl.$^2$ .......................................... C07C 118/02
[52] U.S. Cl. ................................. 260/453 PH; 23/284
[58] Field of Search ................................... 260/453 PH

[56] References Cited

U.S. PATENT DOCUMENTS

| 2,837,554 | 6/1958 | Gemassmer | 260/453 PH |
| 2,908,703 | 10/1959 | Latourette et al. | 260/453 PH |
| 3,226,410 | 12/1965 | Hettich et al. | 260/453 PH |
| 3,234,253 | 2/1966 | Cooper | 260/453 PH |
| 3,574,695 | 4/1971 | Grant, Jr. et al. | 260/453 PH |
| 3,607,903 | 9/1971 | Csuros et al. | 260/453 PH |
| 3,947,484 | 3/1976 | Mitrowsky et al. | 260/453 PH |

*Primary Examiner*—Dolph H. Torrence
*Attorney, Agent, or Firm*—Arthur J. Plantamura; Alan M. Doernberg

[57] ABSTRACT

The reaction of aromatic amines with phosgene takes place in the mixing zone of a plug flow reactor to form both the product isocyanate as well as the intermediate carbamyl chloride. The aromatic amine dissolved in an inert diluent is fed to the center portion of the plug flow reactor while the phosgene is fed to the annular space. The reactor is designed so as to eliminate back-mixing at the feed zone and thus to avoid reaction of any isocyanate formed with the incoming aromatic amine which produces in turn undesirable by-products such as urea and tar. Cold phosgene that is fed into the annular space cools the wall sufficiently to inhibit the reaction to TDI. By heating the wall such as with the installation of a heating jacket to counteract the cooling effect of phosgene, the wall of the reactor is maintained above 90° C. and thus any solid carbamyl chloride that migrates to the wall is reacted to the isocyanate, eliminating pluggage of the reactor from solids build-up.

5 Claims, 3 Drawing Figures

METHOD OF MANUFACTURING AROMATIC ISOCYANATES

BACKGROUND OF THE INVENTION

The reaction of amines with phosgene to produce isocyanates is well known. The reaction may be represented by the following general reaction:

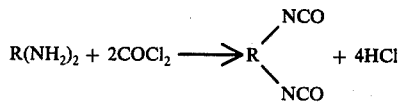

$$R(NH_2)_2 + 2COCl_2 \longrightarrow R\genfrac{}{}{0pt}{}{\diagup NCO}{\diagdown NCO} + 4HCl$$

In the course of the reaction the intermediate carbamyl chloride is formed which has a tendency to react under normal reaction conditions to produce urea and tars which detract substantially from the yield of the desired isocyanate. To avoid the formation of these side products several improvements in the phosgene preparation of isocyanates have been proposed.

One prior art method calls for a two-stage process, the first stage entails the formation of a slurry of intermediates at temperatures ranging from 0° C. to room temperature and subsequently reacting the intermediate products with phosgene at temperatures high enough to convert the intermediate to the isocyanate, usually in the range of 160° to 200° C. This procedure presents processing difficulties due to the release of large amounts of phosgene when the temperature is elevated in the course of the reaction.

Another prior art method is that of U.S. Pat. No. 2,908,703 wherein efforts to minimize by-product formation are by means of a two-stage procedure involving a first stage reaction at a temperature of from about 60° C. to about 90° C. and a second stage wherein intermediate product from the first stage are further reacted.

Still another method attempted is that of U.S. Pat. No. 3,226,410 wherein the patentees describe a continuous process for producing diisocyanates aimed at minimizing backmixing by reacting the phosgene with a dilute stream of the amine carried in an inert organic diluent under superatmospheric pressure in a controlled turbulent flow. None of the known prior art methods have sufficiently reduced the undesirable by-product formation. There is thus a need for a suitable method to increase the yield by minimizing by-products in the manufacture of diisocyanates.

SUMMARY OF THE INVENTION

In accordance with the invention a novel plug flow reactor and process is provided to eliminate backmixing at the feed mixing zone and facilitate the production of diisocyanates with a minimum of undesirable by-products. With the method and arrangement of the invention plugging is essentially eliminated in the reactor mixing zone.

In accordance with the invention, the pluggage in the reactor mixing zone identified as being primarily carbamyl chloride, the intermediate product in the isocyanate reaction is essentially eliminated by regulating the wall temperature of the reactor mixing zone. By thus controlling the temperature, timely and essentially complete conversion of the carbamyl chloride to the desired diisocyanate product takes place before the carbamyl chloride is able to deposit on the wall of the reactor resulting in pluggage of the reactor.

Thus the present invention includes a method of continuously preparing aromatic isocyanates by reacting phosgene in a reactor with an aromatic primary amine under conditions in which an intermediate carbamyl chloride is formed, regulating the reactor wall temperature by supplying sufficient heat to the reactor wall to counteract the cooling effect of additional amounts of phosgene reactant on said intermediate and, by said supplied heat, sustaining the reactor wall at a temperature at which the carbamyl chloride decomposes to aromatic isocyanate and above the reaction temperature prevailing during the formation of said carbamyl chloride, thereby preventing solidification of carbamyl chloride at the reactor wall and producing the desired aromatic isocyanate from the carbamyl chloride.

Regulation of the reaction of the carbamyl chloride in accordance with the invention is effected by controlling the wall temperature and thereby the temperature at which the carbamyl chloride is exposed in the reactor. Preferably a steam jacket is employed for this purpose.

Based on these heat transfer calculations and the fact that carbamyl chloride decomposes to the diisocyanate at temperature of about 90° to 140° C. heating of the reactor wall has been found to prevent pluggage of the reaction zone and undesirable by-product formation while only practical considerations impose an upper temperature limit, generally temperatures between about 90° C. and about 200° C. may be employed.

DETAILED DESCRIPTION OF THE INVENTION

Figure 2:
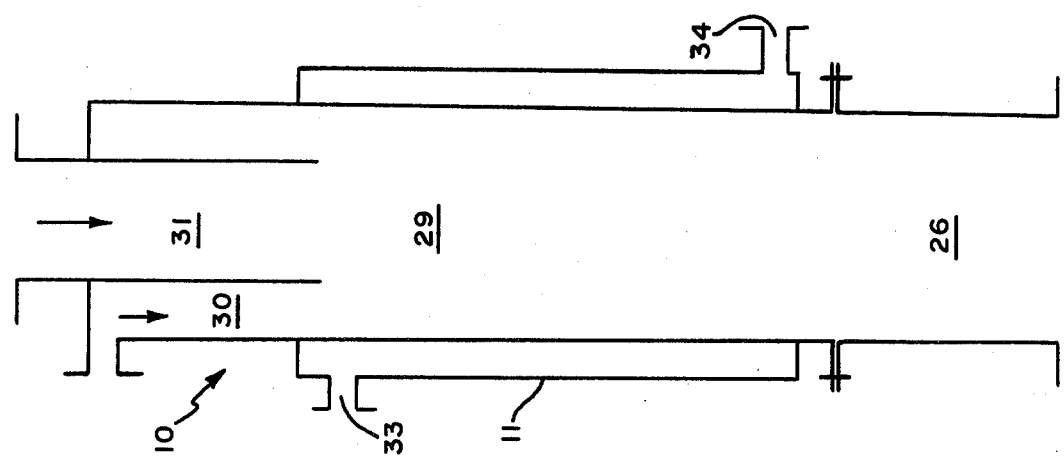
FIG. 2 is a vertical schematic cross-sectional illustration of a reactor of the kind employed in the process of the invention wherein the isocyanate is formed from the phosgene and aromatic amine.

In the description which follows toluenediamine (TDA) will be employed as a typical aromatic amine in describing the invention. However, it will be apparent that various other aromatic amines may also be employed while still retaining the advantages of the invention.

According to the present invention phosgene and an inert organic solvent solution of a primary aromatic amine are reacted together, initially at a temperature between about 60° C. and about 90° C. and subsequently by means of the heat of reaction and secondary backmix reactors. The intermediate reaction mixture is subjected to an elevated temperature sufficiently high to convert the intermediate product to the isocyanate before it can be exposed to reduced temperatures which generate undesirable by-products from the intermediate carbamyl chloride. In the process, aromatic isocyanates are prepared by reacting phosgene with an aromatic primary amine under conditions in which an intermediate carbamyl chloride is formed. Sufficient heat is supplied to the reaction to counteract the cooling effect of the phosgene. The reactor wall temperature is sustained above the temperature prevailing during the subsequent reaction between the carbamyl chloride and phosgene which produces the desired isocyanate.

In a representative embodiment of this invention, a dilute solution of the aromatic amine in an inert organic solvent, such as dichlorobenzene, is passed into the first reactor. Concomitant with the addition of amine solution to the first reactor, phosgene liquid from any convenient source is also admitted to the reactor through a separate entry point. The mass in the reaction vessel is preferably well agitated and sufficient heat is supplied via the exothermic heat of reaction of the amine with phosgene to maintain the preferred temperature for phosgenation.

Preferably, the solution of the amine and the phosgene are introduced at such rates that there is at least a 50% stoichiometric excess of phosgene over that theoretically required to react with the amine.

The process of the invention is preferably carried out continuously and is described by reference to the drawing wherein primed reference numbers are applied in FIG. 3 corresponding, where applicable, to similar components in FIG. 1 bearing the same reference numbers without prime designation.

In the drawing, 24 is a feed tank for the liquid phosgene, provided with the feed line 17 which feeds reactor 10 with the phosgene feed. In FIG. 3, 25 is a feed tank for a solution of phosgene and solvent with a feed line 25' which mixes with the liquid phosgene from line 17' and then fed via line 28' to reactor 10'. 23 and 23' are feed tanks for the amine and 22 and 22' are the solvent feed tanks. The amine fed from line 15 or 15' mixes with the solvent of line 14 or 14' is fed to reactor 10 or 10' via line 16 or 16'. The amine solvent mixture of line 16 or 16' contacts either the phosgene liquid from line 17 or the phosgene and phosgene solvent mixture from line 25' and 17' in the mixing zone 29 of reactor 10. In order to assure good mixing in reactor 10 without backmixing, reactor 10 is sized such that the velocity of stream 28' or 17 in the reactor annular space 30 is lower than the velocity of stream 16 or 16' in the feed tube 31. A velocity ratio of 2.6 to 1 assures good mixing while minimizing backmixing. A heating jacket 11 is provided to maintain the reactor wall temperature above 90° C. to avoid pluggage of the reaction zone. In the heating jacket steam as the heating medium is chosen for convenience, but any suitable heating method can be used such as hot oil in the jacket or heat tracing, steam tracing or electrical tracing, for example. The reaction mass containing a mixture of solvent, intermediate product and isocyanate product is fed through lines 26 or 26' continuously to two secondary backmixed agitated reactors 12, 27 or 12', 27' (FIGS. 1 and 3 respectively) maintained at a temperature of 110° C. to 155° C. to complete the reaction to the desired isocyanate. Excess phosgene and by-product hydrochloric acid are removed from reactors 12, 27 or 12', 27' as a gas, the majority of the phosgene is condensed in condenser 18 or 18' and sent from tank 20 or 20' to the phosgene feed tank 24 or 24' for reuse. The gas stream exits through tank 20 or 20' via line 19 or 19' for further processing to recover the remaining phosgene for reuse and HCl by-product. The reaction mass from reactor 27 or 27' is sent to product purification via line 32 or 32'.

Various aromatic amine primary may be converted to the corresponding isocyanate by this process. The amine may be a monoamine, a diamine or some other polyamine. Examples of aromatic amines which may be used in the practice of this invention are aniline, the isomeric toluidines, the isomeric xylidines, o-, m-, and p-alkylanilines, o-, m-, amd p-chloroanilines, the isomeric dichloroanilines, the isomeric phenylenediamines, the isomeric diaminotoluenes, the isomeric diaminoxylenes, various diaminoalkyl benzenes, alpha- and beta naphthylamines, the isomeric diaminonaphthalenes, the isomeric bisaminophenylmethanes, the isomeric trisaminophenylmethanes, the dianisidines the diaminodiphenyls and mixtures of these amines. The amine should be free of groups which would interfere with the reaction between the amino group and phosgene or with the isocyanate radical, that contain active hydrogen atoms. Such groups are, for example, —OH, —COOH, —SH, etc. The most preferred diamine is toluenediamine.

The initial temperatures of phosgenation employed in this invention range from about 60° C. to about 90° C. The preferred temperatures in this range are from 65° to 80° C.

30 pounds per square inch gage pressure is normally employed as a matter of convenience, though higher or lower pressure may be used.

The solvents employed in this process are those which are inert to the reactants and products. Although aliphatic and aromatic hydrocarbons which are inert to the reactants and products, are satisfactory solvents, the preferred solvents are the chlorinated hydrocarbons. Representative members of this class are monochlorobenzene, dichlorobenzene, carbon tetrachloride, the corresponding chlorinated toluenes and xylenes and trichloroethylene. The most preferred solvent is dichlorobenzene. It is desirable and preferable to choose a solvent that boils lower than the isocyanate product.

The amine may be introduced into the reaction vessel in solution in the chlorinated hydrocarbon solvent. Concentrations of the amine may be varied from about 2 to 20% by weight of the solution. The reaction will proceed at lower concentrations; however, lower concentrations result in uneconomically low volume productivities. Higher concentrations of the amine lead to formation of undesirable side products, i.e., urea, substituted ureas, polyureas and tar compounds The preferred range of the amine solution is 5 to 10% by weight of amine.

The concentration of phosgene in the reaction solution is regulated by the temperature being employed for the reaction. Preferably, an essentially saturated solution of phosgene in the solvent should be maintained at all times during the reaction. Low concentrations of phosgene result in decreased efficiencies, due to formation of side products. The use of greater amounts of phosgene does not adversely affect the efficiency of the operation. However, it will be apparent that precautions must be taken to handle the excess phosgene and, thus, large excesses of phosgene are to be avoided.

The advantages and mode of carrying out the process of this invention are further illustrated by the following representative examples:

EXAMPLE I

Figure 1:
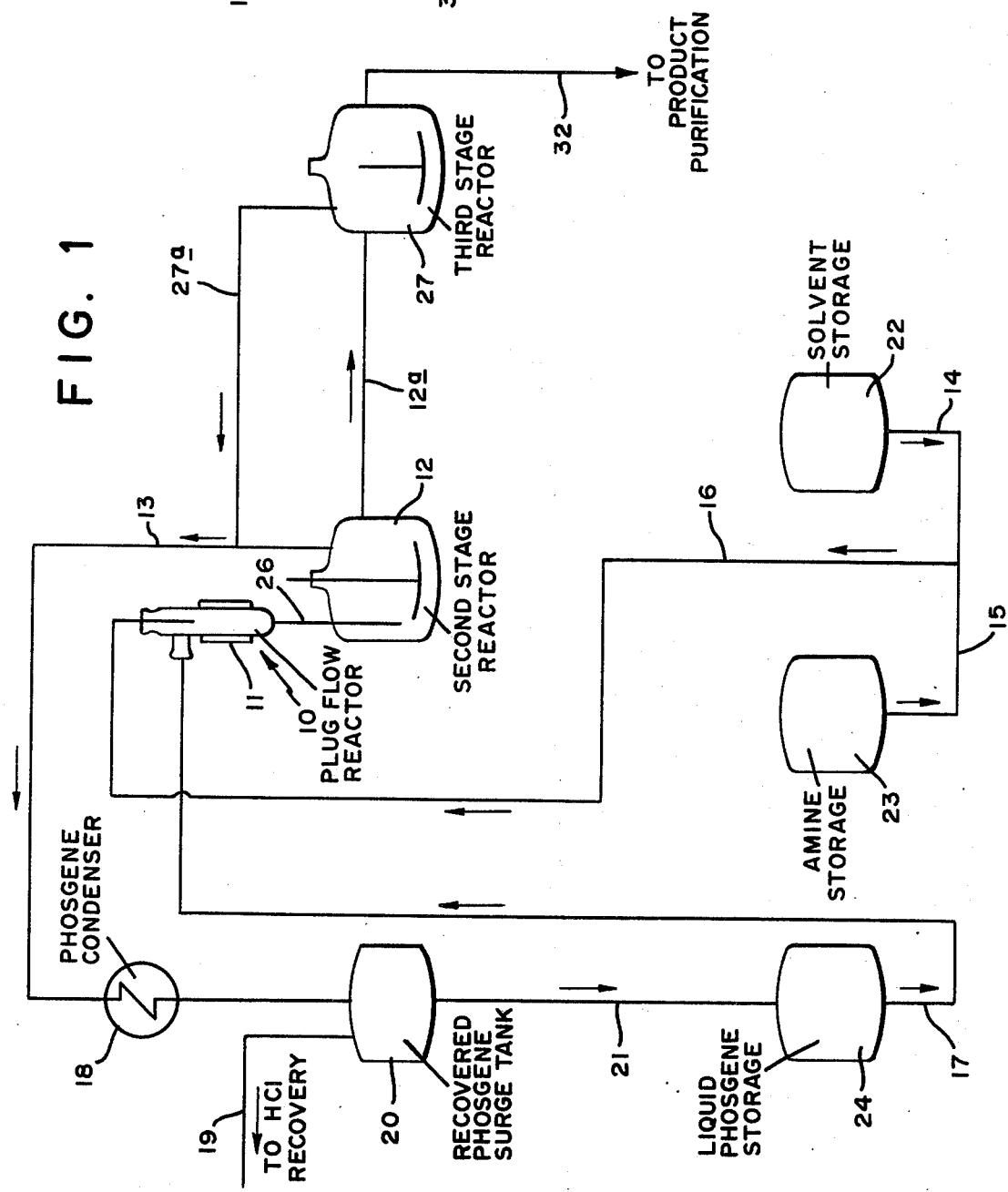
FIG. 1 is a flow diagram illustrating a preferred scheme for production of diisocyanate utilizing the improved reactor arrangement and process of the invention.

Referring to FIGS. 1 and 2, 100 pounds per hour of toulenediamine are mixed with 900 pounds per hour of dichlorobenzene at 60° C. and sent to reactor 10. Simultaneously, 365 pounds per hour of phosgene at 0° C. is pumped to reactor 10. Reactor 10 is so sized that a velocity ratio of 2.6 to 1 is maintained between the toluenediamine, dichlorobenzene mixture and the phosgene entering the reaction zone 29.

The reaction proceeds adiabatically with the reaction mass exiting the reactor at a temperature of 110° C. via stream 26. Steam is added to the jacket at point 33 to maintain the wall temperature of reactor 10 at 90° C. The reactor 10 is run at a pressure of 30 psig.

The reaction to the diisocyanate is completed in reactor 12 and 27. Reactor 12 being maintained at 110° C. and reactor 27 being maintained at 145° C. Phosgene and by-product HCl along with trace amounts of product isocyanate are taken overhead in stream 13. Stream 13 consists of 182.6 pounds per hour phosgene and 116.6 pounds per hour HCl. The phosgene is recovered from the HCl by condensation and 182.6 pounds per hour are sent to tank 20. 116.6 pounds per hour of HCl is recovered as aqueous HCl in standard equipment. 1065.8 pounds per hour of reaction products are removed via line 32. This reaction product consists of 3.1 pounds per hour HCl, 20.3 pounds per hour phosgene, 900 pounds per hour dichlorobenzene, 130.5 pounds per hour toluene diisocyanate and 11.9 pounds of reaction by-product. The product toluene diisocyanate is purified by fractional distillation. The yield of toluene diisocyanate is approximately 91% based on the amine.

EXAMPLE II

Figure 3:
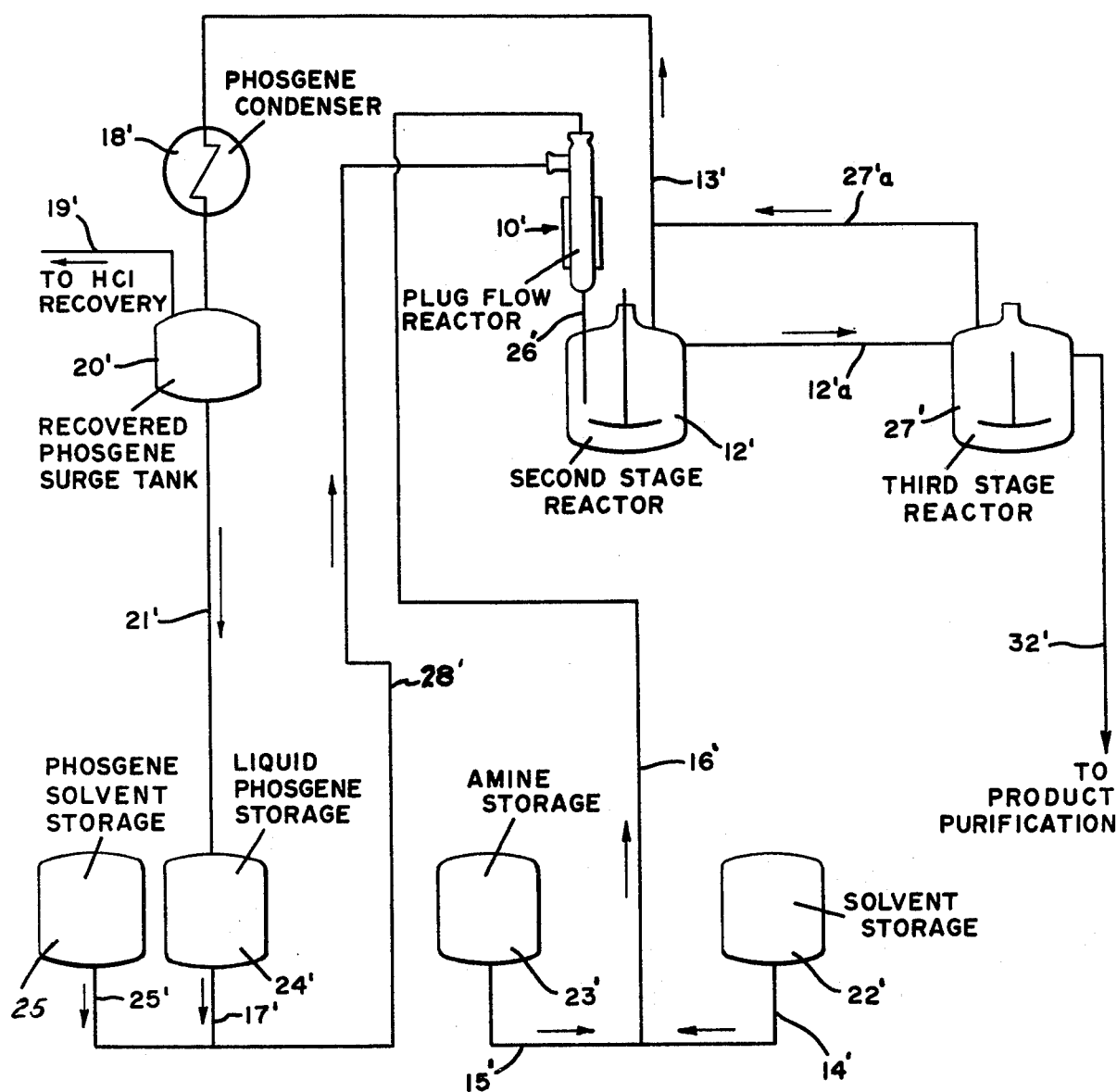
FIG. 3 is a flow diagram similar to FIG. 1 illustrating an alternate scheme in accordance with the invention.

Referring to FIGS. 2 and 3, 100 pounds per hour of toluenediamine are mixed with 540 pounds per hour of dichlorobenzene at 60° C. and sent to reactor 10'. Simultaneously, 301 pounds per hour of phosgene is mixed with a solution containing 360 pounds per hour dichlorobenzene and 64 pounds per hour phosgene and is sent to reactor 10' via line 28. The mixture is at 0° C. Reactor 10' is so sized such that a velocity ratio of 2.6 to 1 is maintained between the toluenediamine, dichlorobenzene mixture and the phosgene, dichlorobenzene mixture entering the reaction zone 29.

The reaction proceeds adiabatically with the reaction mass exiting the reactor at a temperature of 110° C. via stream 26. Steam is added to the jacket at point 33 to maintain the wall temperature of reactor 10 at 90° C. The reactor 10' is run at a pressure of 30 psig.

The reaction to the diisocyanate is completed in reactor 12' and 27'. Reactor 12' being maintained at 110° C. and reactor 27' being maintained at 145° C. Phosgene and by-product HCl along with trace amounts of product isocyanate are taken overhead in stream 13'. Stream 13' consists of 182.6 pounds per hour phosgene and 116.6 pounds per hour HCl. The phogene is recovered from the HCl by condensation and 182.6 pounds per hour are sent to tank 20'. 116.6 pounds per hour of HCl is recovered as aqueous HCl in standard equipment. 1065.8 pounds per hour of reaction products are removed via line 32'. This reaction product consists of 3.1 pounds per hour HCl, 20.3 pounds per hour phosgene, 900 pounds per hour dichlorobenzene, 130.5 pounds per hour toulene diisocyanate and 11.9 pounds of reaction by-product. The product toluene diisocyanate is purified by fractional distillation. The yield of toluene diisocyanate is approximately the same as Example I based on the amine.

It will be apparent that various changes may be incorporated in the foregoing procedure without departing from the scope of the invention and that unless specifically limited in the appended claims the details supplied in the description as shown in the drawing are to be interpreted as illustrative and not limiting.

What is claimed is:

1. A method of continuously preparing aromatic isocyanates by reacting phosgene in a reactor with an aromatic primary amine under conditions in which an intermediate carbamyl chloride is formed, regulating the reactor wall temperature by supplying sufficient heat to the reactor wall to counteract the cooling effect of additional amounts of phosgene reactant on said intermediate and, by said supplied heat, sustaining the reactor wall temperature at a temperature at which the carbamyl chloride decomposes to aromatic isocyanate and above the reaction temperature prevailing during the formation of said carbamyl chloride, thereby preventing solidification of carbamyl chloride at the reactor wall and producing the desired aromatic isocyanate from the carbamyl chloride.

2. The method of claim 1 wherein the primary amine is a diamine.

3. The method of claim 1 wherein the primary amine is toluenediamine.

4. The method of claim 3 wherein said reactor wall temperature is above about 90° C.

5. The method of claim 4 wherein the phosgene is reacted with the aromatic primary amine at a temperature between about 60° C and about 90° C.

* * * * *